(12) United States Patent
Ditmarsen et al.

(10) Patent No.: US 6,236,048 B1
(45) Date of Patent: May 22, 2001

(54) APPARATUS FOR INVESTIGATING FLOWABLE MATERIAL AND DEVICE FOR CONVEYING SAMPLES

(75) Inventors: Jan Ditmarsen, Glostrup; Hilmer Jensen, Skælskør; Freddy Petersen, Jyllinge; Claus Borggaard, Viby Sj.; Jens Havn Thorup, København N, all of (DK)

(73) Assignee: Wolfking Danmark A/S, Slagelse (DK)

( * ) Notice: Subject to any disclaimer, the term of this patent is extended or adjusted under 35 U.S.C. 154(b) by 0 days.

(21) Appl. No.: 09/466,511

(22) Filed: Dec. 17, 1999

Related U.S. Application Data

(63) Continuation of application No. 08/875,877, filed as application No. PCT/DK96/00066 on Feb. 20, 1996, now Pat. No. 6,020,588.

(30) Foreign Application Priority Data

Feb. 10, 1995 (DK) .................................................. 0155/95
Jan. 26, 1996 (DK) .................................................. 0090/96

(51) Int. Cl.[7] ........................... G01N 21/35; G01N 33/12
(52) U.S. Cl. .................................. 250/339.12; 73/863.57
(58) Field of Search ....................... 73/863.57; 250/339.12

(56) References Cited

U.S. PATENT DOCUMENTS

| 4,451,152 | 5/1984 | Topol et al. . |
|---|---|---|
| 4,563,581 | 1/1986 | Perten . |
| 4,627,008 | 12/1986 | Rosenthal . |
| 4,640,614 | * 2/1987 | Roberts et al. ........................ 356/36 |
| 5,065,416 | 11/1991 | Laurila et al. . |
| 5,241,178 | 8/1993 | Shields . |
| 6,020,588 | * 2/2000 | Ditmarsen et al. ............. 250/339.12 |

FOREIGN PATENT DOCUMENTS

| 0 182 564 | 5/1986 | (EP) . |
|---|---|---|
| 0 388 082 | 9/1990 | (EP) . |

* cited by examiner

*Primary Examiner*—Constantine Hannaher
(74) *Attorney, Agent, or Firm*—Pennie & Edmonds LLP

(57) ABSTRACT

An apparatus for examining a flowable material comprises a tube having an opening for receiving material and an opening for discharging material. Further, the tube comprises a segment adapted for making measurements. Adjacent the tube section there is a measuring device having a light source on one side for transmitting light into the segment and a light receiver on the opposite side to measure the effect upon the light of a material placed in the segment. At the beam path between the light source and the light receiver, the walls of the tube segment are made of a material being translucent or transparent to the range of light wavelengths to be examined. A recording unit connected to the measuring device records individual measurement values or sets of same on material placed in the tube segment. Samples may be conveyed through the apparatus by means of a device comprising a tube having an opening for receiving a material and an opening for discharging material as well as a tube segment adapted for making measurements. A movable closure means is placed in the tube at the opening for receiving material, and a conveying member conveys the material having been received into the tube segment adapted for making measurements.

21 Claims, 6 Drawing Sheets

APPARATUS FOR INVESTIGATING FLOWABLE MATERIAL AND DEVICE FOR CONVEYING SAMPLES

CROSS-REFERENCE TO RELATED APPLICATIONS

This application is a continuation of application Ser. No. 08/875,877 filed Aug. 6, 1997 now U.S. Pat. No. 6,020,588 which is a 371 of PCT/DK96/00066 Feb. 20, 1996.

FIELD OF THE INVENTION

The present invention relates to an apparatus for examining a flowable material.

BACKGROUND OF THE INVENTION

The expression "near-infra-red spectroscopy" is used to designate methods of measurements based upon the interaction between matter and electromagnetic radiation in the wavelength range from 700 to 2500 nm. The reason for using this expression is that it refers to the part of the infra-red wavelength range lying closest to the visual range of the spectrum (400 to 700 nm). In the literature, the expression "near-near-infra-red range" is used for electromagnetic radiation with wavelengths from 700 to 1200 nm.

Near-infra-red spectroscopy is used for determining components of various materials, e.g. in meat products. Meat consists substantially of water, protein and fat. Each type of chemical bond such as O—H, C—H, C=O, C—N, N—H, absorbs light at wavelengths characteristic for the molecule part concerned. The cause of the absorption is that two different atoms being bonded to each other function in the manner of an electric dipole taking energy from the electric and magnetic fields in the radiation, making the group of atoms concerned vibrate. Thus, a C=O bond in a triglyceride will absorb light at a wavelength, that is different from that absorbed by a C=O bond in a protein molecule. By measuring how much the light is attenuated by passing through a sample of meat at one of these characteristic wavelengths it is possible to determine the percentage of a component of the meat.

Measurements in the near-infra-red range may be carried out in two ways, either by passing light through the sample (near-infra-red transmission, NIT) or based on the reflection from the surface of the sample (near-infra-red reflection, NIR). In samples with a high water content, such as meat, NIT cannot be used when making measurements above 1300 nm, because the absorption by the water molecules is far too strong at longer wavelengths. With measurements based upon the reflection there is the disadvantage that they have to be carried out either on a free surface, which is not well-defined, or through a glass window. In the latter case, it cannot be avoided that fat on the comminuted meat adheres to the inside of the glass window, possibly causing erroneous measurement. Further, due to the small measuring volume, measurements based on reflection will not be as representative as NIT measurements.

Various analysis apparatus for examining materials by means of NIT spectroscopy are known. One of these apparatuses comprises a number of cups, in which a homogenized sample is placed. Then, the absorption of the sample is measured at a number of different wavelengths, and the content of components is computed on the basis of the absorption values having been found. The apparatus is extremely complicated to use. Thus, it is necessary to take a sample that is representative of the material to be examined, then the sample has to be homogenized, and finally the homogenized material has to be placed in the cups of the apparatus using great care. After this, the analysis may be carried out.

SUMMARY OF THE INVENTION

It is the object of the present invention to provide an apparatus for examining a flowable material, with which it is possible to exploit the advantages associated with spectroscopy, but which is not so complicated to use as the previously known apparatus referred to above. Preferably, the apparatus according to the invention should operate automatically without the need for the preparatory work referred to above (manual taking of a representative sample quantity, preparing a homogenized sample and placing in cups). The apparatus according to the present invention is characterized by comprising a tube having an opening for receiving material and an opening for discharging material as well as a tube segment adapted for making measurements, a measuring device placed adjacent said tube segment and having a light source on one side of the tube segment to transmit light into the segment and a light receiver on the opposite side of the segment to measure the effect upon the light of a material placed in the segment, the walls of the tube segment comprising the beam path between the light source and the light receiver being made of a material that is translucent or transparent for the wavelength range of the light to be examined, and a recording unit connected to said measuring device and adapted to record individual measurement values or sets of same for material having been placed in said tube segment.

DETAILED DESCRIPTION OF THE INVENTION

Figure 2:
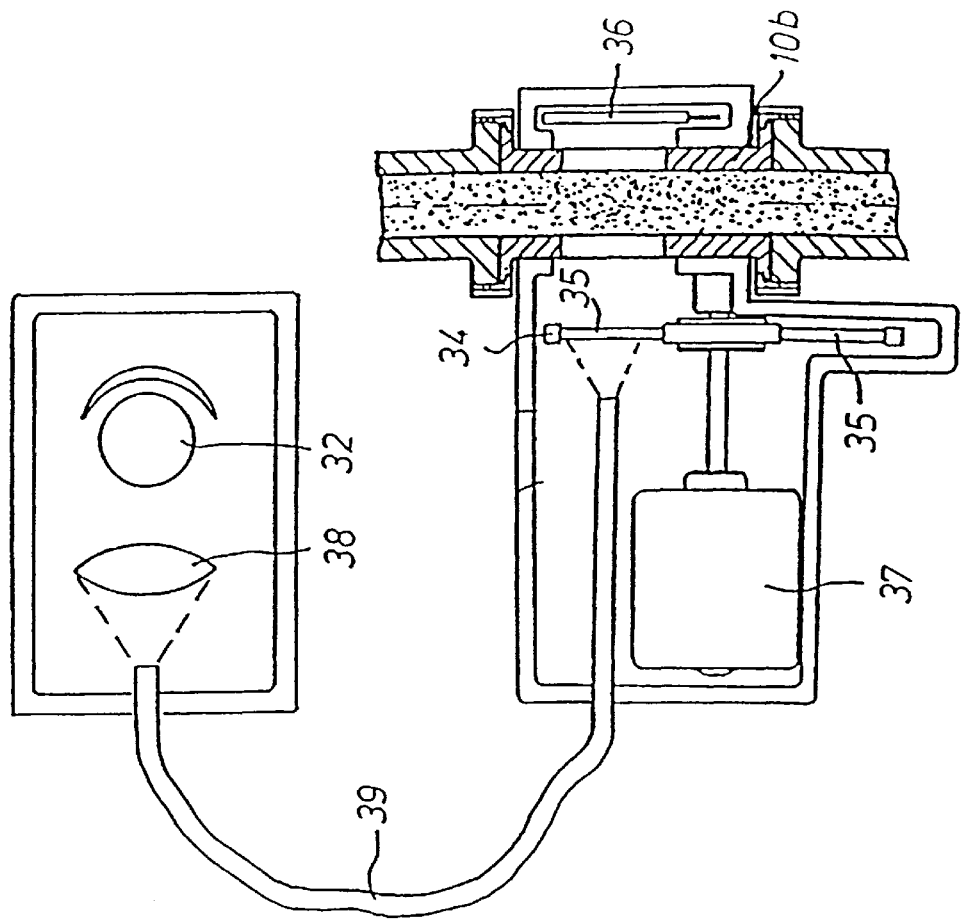
FIG. 2 shows an embodiment of the invention wherein the light source is in a separate enclosure.

With the apparatus according to the present invention, there is no requirement for the sample to be liquid or homogeneous, such as is the case with the previously known apparatus. It is only required that the sample be flowable, so that it can pass through a tube. In this connection, the taking of samples and the analysis of the material can be carried out automatically, also in those cases, in which the sample is inhomogeneous. For this reason, the apparatus does not require operators skilled in taking a sample of the material or judging whether a sample quantity is representative. It is only necessary to dimension the measuring equipment for relatively small sizes of samples, as the sampling and measuring is merely repeated, until the sum total of the measurements is representative and provides the desired accuracy of measurement. In other words: the mechanical parts may be small, and it is still possible to adjust the total volume of material being measured to what is optimum or desired in each case. Surprisingly, it has been found possible with the NIT analysis described to carry out measurements on relatively large quantities of an inhomogeneous material for each measuring cycle, so that a limited number of measurements may be sufficient and the method hence also becoming practically useful for making measurements on unprocessed and inhomogeneous materials.

The content of components in the material may be monitored continuously by automatic and repeated analysis of new samples. This makes it possible to use the apparatus according to the invention for determining the moment in time, at which a material possesses a requisite property, e.g. uniformity with regard to components.

Plants already having been installed in establishments for the production and/or processing of various materials can be made to give an increased yield when supplemented with an analysis apparatus according to the present invention.

The apparatus according to the present invention may be used in connection with flowable materials, whether these be in the form of particles or liquids. It is especially advantageous to use the apparatus in connection with non-uniform material, e.g. consisting of components of different compositions, because the apparatus does not require the samples to be homogenized in order to achieve reliable results. The apparatus is especially useful for examining foodstuffs, fodder and pharmaceutical materials.

Such materials may e.g. include:

vegetable foods, such a wheat, barley, rye, maize, rice, coffee and cocoa in the form of whole grains or a ground or comminuted product (analysis for protein, starch, carbohydrate and/or water), seeds, e.g. peas and beans, such as soy beans (analysis for protein, fats and/or water), products mainly consisting of or extracted from vegetable raw materials, such as snacks, dough, vegetable mixtures, margarine, edible oils, fibre products, chocolate, sugar, syrup, lozenges and dried coffee extract (powder/granulate), animal foodstuffs, such as dairy produce, e.g. milk, yoghurt and other soured milk products, ice cream, cheese (analysis for protein, carbohydrate, lactose, fat and/or water), meat products, e.g. meat of pork, beef, mutton, poultry and fish in the form of minced or emulgated products (analysis for protein, fat, water and/or salts) and eggs, which foodstuffs may be present in a completely or partly frozen condition, fodder, e.g. pellets or dry/wet fodder mixtures of vegetable products, fats and protein-containing raw materials, including pet food, pharmaceutical products, such as tablets, mixtures, creams and ointments, and technical substances, e.g. wet and dry mixtures of cement and mortar, plastics, e.g. in granular form, mineral materials, such as solvents and petrochemical products, e.g. oils, hydrocarbons and asphalt, solutions of organic or inorganic substances, e.g. sugar solutions.

The material being present in the tube segment during a measurement may constitute a quantity that is not representative for the determination of one or a number of components of a greater quantity of material, from which the sample has been taken, e.g. a mixing tank or tub. If it is required, the content of one or a number of components in such a larger quantity of material may be determined by repeating the measuring procedure so many times with new material being introduced in the tube segment, that the sum total of the quantities of material being measured in the tube section constitutes a representative quantity.

It is also possible to carry out continuous measurements of the contents of the material, e.g. in connection with controlling a process or monitoring a material flow. The tube segment may e.g. be inserted in a tube through which the material flows, or in a branch or loop on such a tube.

The apparatus preferably operates with a non-destructive sampling and analysis, in which the sample material is returned or advanced in an unharmed state. For this reason, it is preferred in the tube segment to introduce material that is substantially unchanged relative to the base material with regard to components and possible particle size, and after carrying out the measurement, the material may be returned in a substantially unharmed condition.

The steps of taking samples from a tank or tub, a tube or the like, introducing samples having been taken into the tube segment, and measuring the effect of the material on light, are preferably carried out whilst the material is in movement, as this may contribute to a correct sampling.

It is also possible to carry out the measurements while the material in the tube segment is at rest, thus also making it possible to use measuring methods requiring relatively long measuring times. The material may, however, also be in movement during the measuring step.

For detecting the near-infra-red radiation, the following materials may be used:

Si: A very sensitive and cheap detector type, useful in the range from 400 to 1100 nm.

Ge: Hardly as sensitive as Si, but is useful from 800 to 1800 nm.

InGaAs: Only half as sensitive as Si, but reacts very quickly and is useful from 800 to 1760 nm.

PbS: Low sensitivity, but is cheap and is useful from 650 to 3000 nm. Temperature stabilization is required.

PMT (Photo-Multiplier Tube): This is by far the most sensitive type of detector.

Measurements on natural products have shown that there is not always any linear correlation between the light absorption and the percentage of a component in the sample. The absorbance is not solely due to the presence of absorbing compounds in the sample, but is also influenced by the dispersion of light in the sample. It is also necessary to take account of the fact that the composition of natural products is so complicated, that absorptions caused by different compounds or functional groups overlap each other in the spectrum. In this connection it is consequently possible to use more complicated mathematical models, e.g. neural networks or classical statistical methods, for determining the content of a compound in the sample on the basis of the resulting measurement values.

In this connection, tests with comminuted meat raw materials on an NIT analysis instrument have shown that the content of the three main components fat, water and protein may be determined, even in the situation in which they do not add up to 100% due to the presence of other additives.

An embodiment of the apparatus according to the invention consists in that the measuring device is adapted to measure the effect of the material upon light in the near-infra-red interval, preferably transmission of near-infra-red light (NIT) through a material being placed in said tube segment.

Preferably the measuring device is adapted to measure the transmittance or absorbance of a material placed in said tube segment at a number of wavelengths in the range from 700 to 2400 nm, preferably 10 or more wavelengths, especially in the near-near-infra-red interval from 700 to 1200 nm. The content of one or a number of components of the material can be determined on the basis of the measurement values or sets of same having been recorded.

It has been found that NIT measurements may also be used for determining the particle size of the material in the tube. In accordance with this the transmittance or absorbance of a particulate material placed in said tube segment may be measured at a number of wavelengths in the range from 700 to 2400 nm, especially 700 to 1200 nm, after which the particle size of the material can be determined on the basis of the measurement values or sets of same having been recorded.

Thus, it is possible to use the recorded measurement values or sets of same to ascertain whether or when a mixture or a stream of material is sufficiently homogeneous or fulfils certain specifications with regard to content and/or particle size.

The measurement values may be used for adjusting the composition of a greater quantity of material. The content of one or a number of components of samples of the material is determined on the basis of the recorded measurement values or sets of same, and the results or their deviation from desired values or information about necessary addition of a component to the bulk of material in order to achieve a desired value is shown on a display and/or used for controlling a dosing unit adapted to make up for the deficiency of a component, e.g. by adding the requisite quantity to the bulk of material in a mixing tank.

The apparatus according to the present invention may be adapted to measure the transmittance or absorbance of a particulate material, e.g. a minced or cut meat product with an average particle size of between 2 and 30 mm at a number of wavelengths in the near-infra-red range, preferably between 700 and 1200 nm, and to use recorded measurement values or sets of same for determining the content of one or a number of components of the material, e.g. in a meat product, preferably its content of fat, protein, collagen and/or water,
   for determining the particle size of the material, and/or
   to ascertain whether or when a mixture or a stream of material is sufficiently homogeneous with regard to one or a number of components and/or particle size.

In this manner it is possible to control or determine not less than three different parameters being of substantial significance for a satisfactory mixing process.

Preferably, the tube and the measuring device are constructed and dimensioned in such a manner, that the volume of the material being subjected to measurements is greater than 20 cm$^3$, preferably greater than 50 cm$^3$ and particularly greater than 100 cm$^3$. By operating on such larger volumes, the fluctuations in the measurements caused by inhomogeneities in the components and/or particle size of the material will be reduced. With such larger measuring volumes, it is in some cases possible to carry out the measurements directly on a material stream in production, so that taking of samples as such may be avoided.

Preferably the tube is dimensioned in such a manner, that the path length of the light rays through the material exceeds 25 mm, preferably lying between 40 and 100 mm. Up to the present moment, no apparatus has been available that is capable of carrying out NIT spectroscopy with such large thicknesses of material.

Preferably the light receiver is a detector plate sensitive for light in a wide spectrum, preferably all of the wavelength range to be examined, prefeably having an effective area exceeding 500 mm$^2$, especially lying between 500 and 10000 mm$^2$. The expression "effective area" refers to the area receiving light from the light source.

Such a detector with a wide spectral range may be used for determining the transmittance or absorbance at a number of different wavelength intervals. The relatively large surface area increases the signal-to-noise ratio. At the same time, the measuring volume becomes large, so that fluctuations or inhomogeneities in the material are evened out, and a representative sample quantity is provided more quickly.

The detector may consist of a number of smaller plates of e.g. 100–200 mm$^2$ being inter-connected to act as one large detector plate. The plate is preferably used without lenses or similar optical systems in front, that would otherwise attenuate the light and limit the field of vision of the plate.

Preferably the detector plate with its fittings is placed directly on the tube, whereby a large field of vision and small losses of light are achieved.

One embodiment according to the invention is characterized in that the light source and the light receiver are of the wide-spectrum type, and that in the beam path between the light source and the light receiver there is placed a rotatable filter disc with cut-outs placed about its shaft at uniform distances, in which cut-outs filters are inserted, each allowing a respective wavelength interval to pass, whereby one filter at a time can be placed in the beam path by means of a motor connected to the shaft of the filter disc.

In an alternative embodiment, the light source consists of a number of narrow-band light sources, each emitting light in a respective wavelength interval, preferably 4–20 monochromatic laser diodes placed on one side of the tube segment, each emitting a respective wavelength interval within the range between 700 and 1200 nm.

The light source may comprise a light-conducting cable, so that the light-producing part can be placed in a separate cabinet separate from the measuring device. The heating effect is reduced and a certain focusing of the light is achieved. Similarly, the detector may comprise a light-conducting cable, such that the detector may be placed in a separate cabinet.

The apparatus according to the invention may comprise a control unit to cause the repetition of a measuring procedure comprising the introduction of new material in the tube segment and measurement of the effect of the material upon the light.

Optimum measuring conditions may e.g. be achieved by using the apparatus to carry out the near-infra-red measurements with a physical path length in the measuring tube of e.g. 40 to 60 mm, by having the sample remain stationary during the fraction of a second in which the measuring is carried out, and by having the sample being as free from air pockets as possible during the measuring process; this may be achieved by means of compression.

The present invention also relates to a device for conveying samples in connection with the examination of flowable material. This device comprises a tube having an opening for receiving a material, an opening for discharging material and a tube segment adapted for making measurements; a movable closure means placed in the tube at the opening for receiving material, and a conveying means to move material having been received into the tube segment adapted for making measurements.

By using this device, it is possible to automatically take a sample and place it in the measuring space of an analysis equipment.

The closure means may be adapted to be opened in connection with the reception of material and to be closed in connection with the conveying of material having been received toward said tube segment. This will prevent the sample from changing during the measuring process, e.g. by flowing back.

The device may comprise a second closure means in the tube on the same side of said tube segment as the discharge opening, said second closure means being adapted to be closed during a period while the conveying means introduces new material into the tube segment, and to open when material having been examined is to be moved out of the tube segment. Hereby it is possible to compress the material during the measuring process, after which the material may be pressed out from the measuring region.

The conveying means is preferably a plunger adapted to slide in a fluid-tight manner along the inside of the tube. Hereby it is possible to a high degree to avoid the smear problems known from worm conveyors, that would otherwise produce a film of fat on windows and the like, disturbing the measurements.

The device preferably comprises one or a number of pneumatic cylinders with pistons to act upon the conveying means and/or the closing means in the tube.

The device may be adapted to compress the material in the tube segment before the examination is carried out, preferably to a pressure of between 200 and 2000 kPa (2 and 20 bar). Hereby it is possible to compress or dissolve any bubbles of air or gas being present in the material, thus normally improving the accuracy of measurement and simplifying the measuring operation.

When in the present description, "particles" or "grains" are referred to, their sizes are preferably 1 mm or more, especially 3 mm or more, the material especially being present in its natural form, e.g. as a natural product, or as a material only having been subjected to coarse comminution, i.e. not in a finely comminuted or homogenized form.

Figure 1:
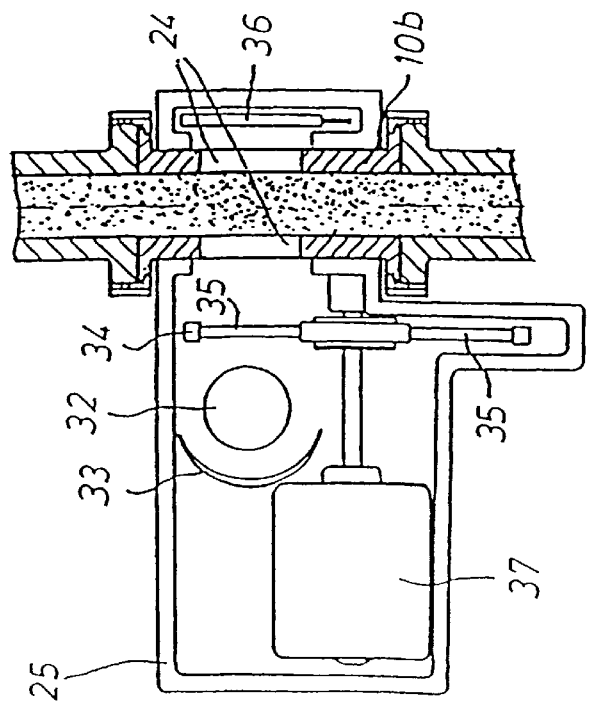
FIG. 1 shows an embodiment of the invention adapted to examine meat material.
Figure 4:
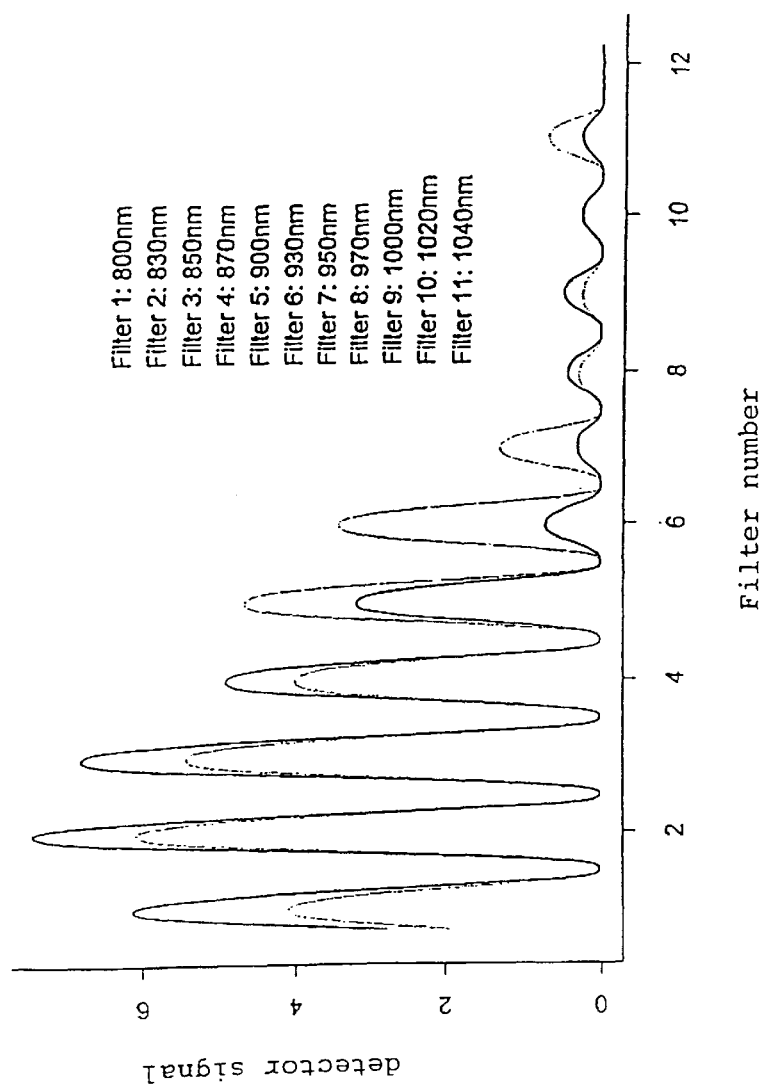
FIG. 4 shows representative signal from a detector.
Figure 3:
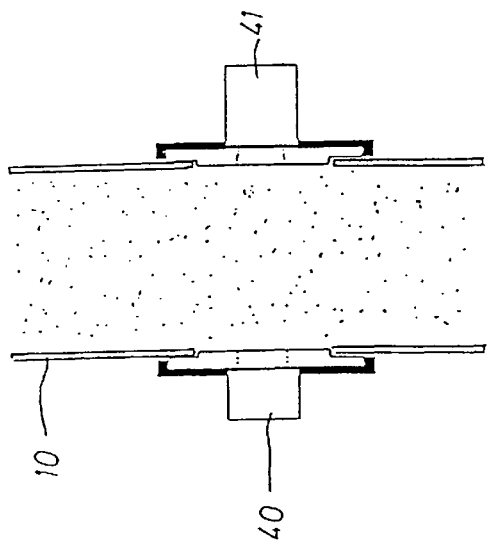
FIG. 3 shows an arrangement of laser diodes adapted to emit light toward the sample.
Figure 5C:
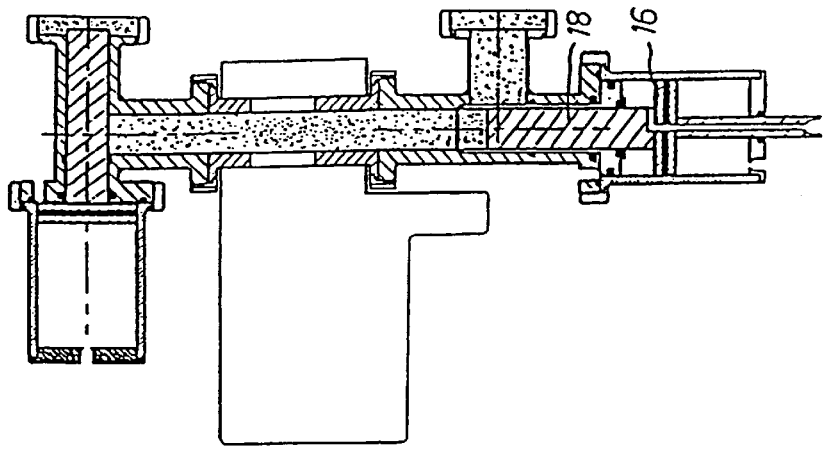
FIGS. 5a to 5f show an embodiment of the invention adapted to introduce and remove material from the tube.
Figure 5B:
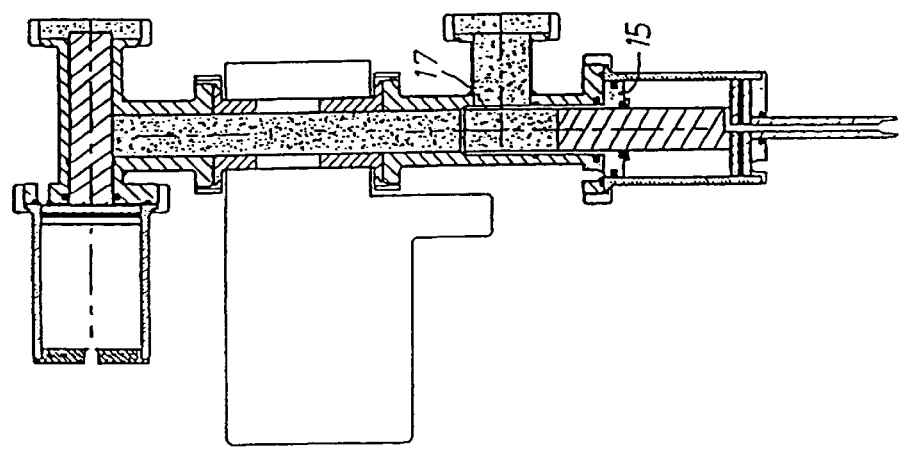
Figure 5A:
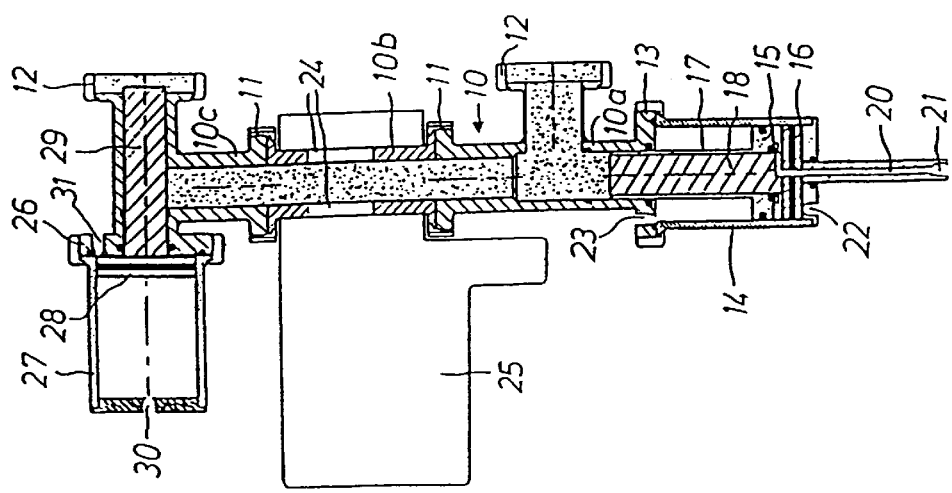
Figure 5F:
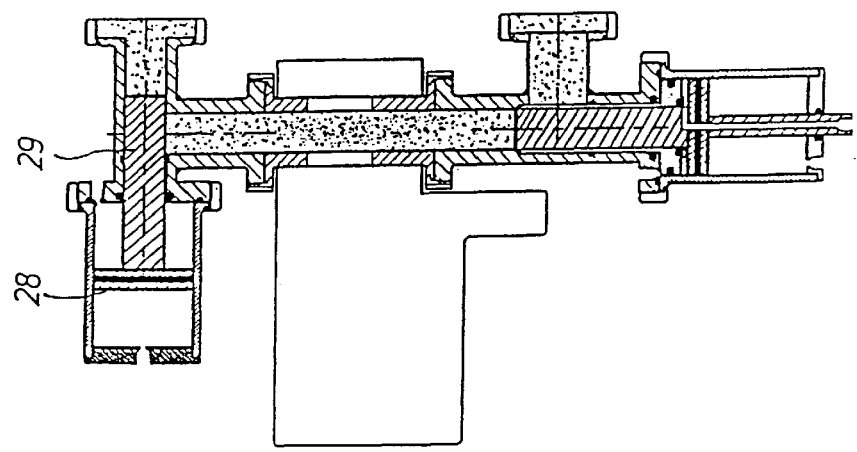
Figure 5E:
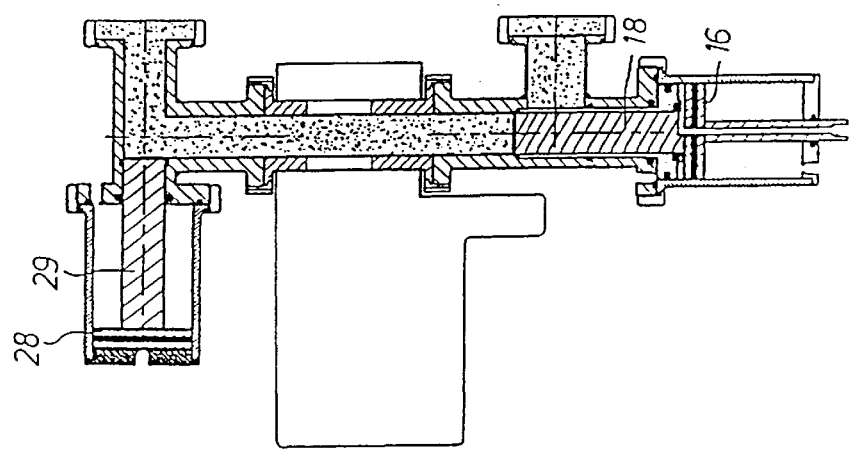
Figure 5D:
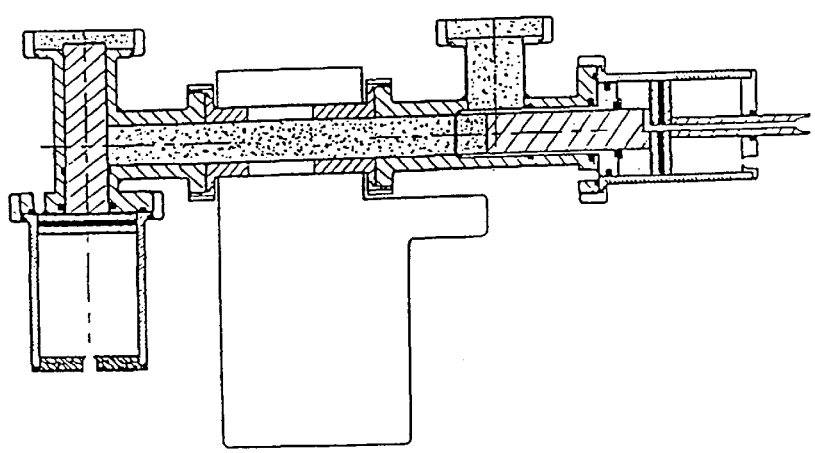
Figure 6:
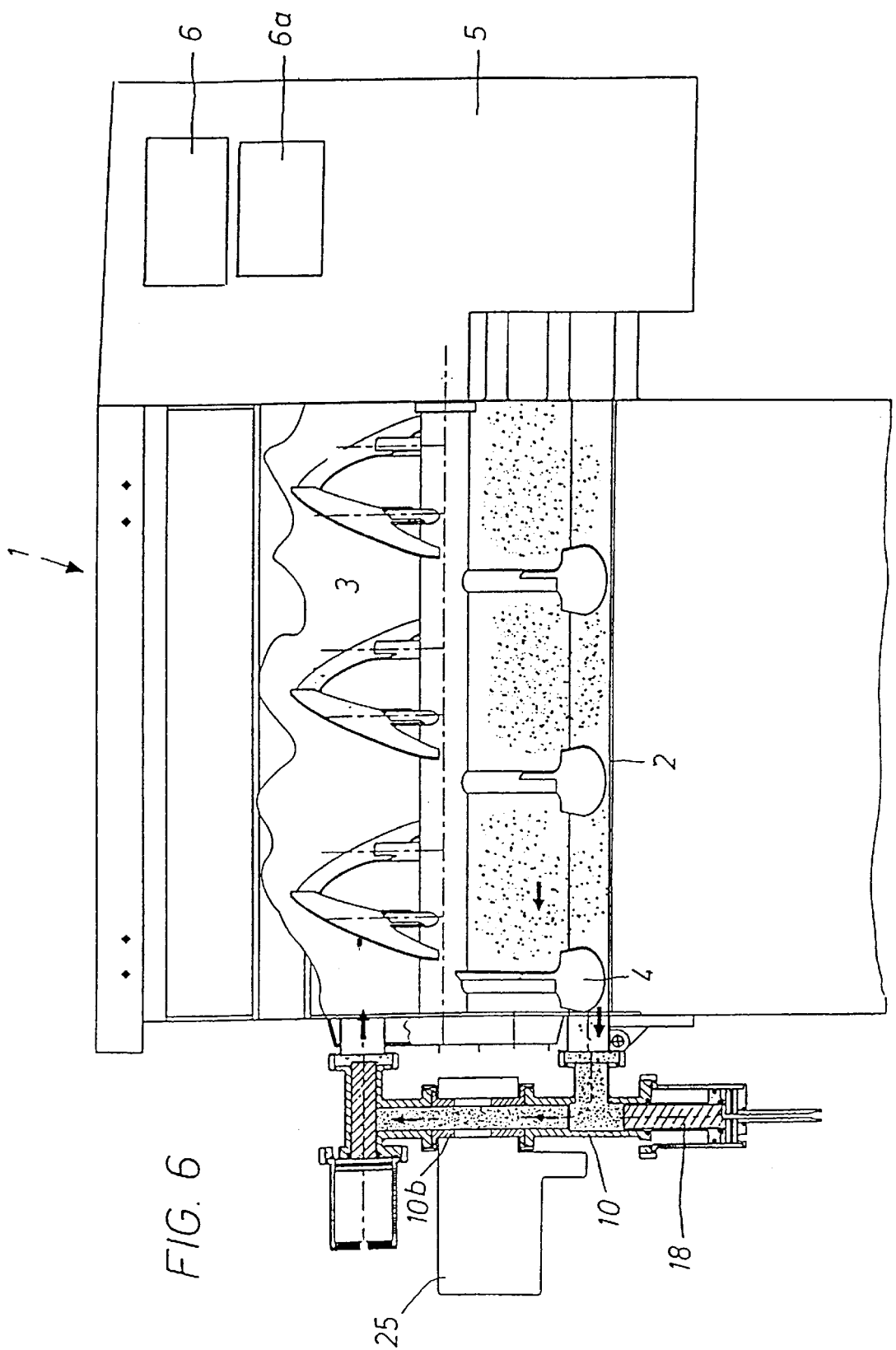
FIGS. 6 and 7 show embodiments of the invention as they may be incorporated in a manufacturing plant.
Figure 7:
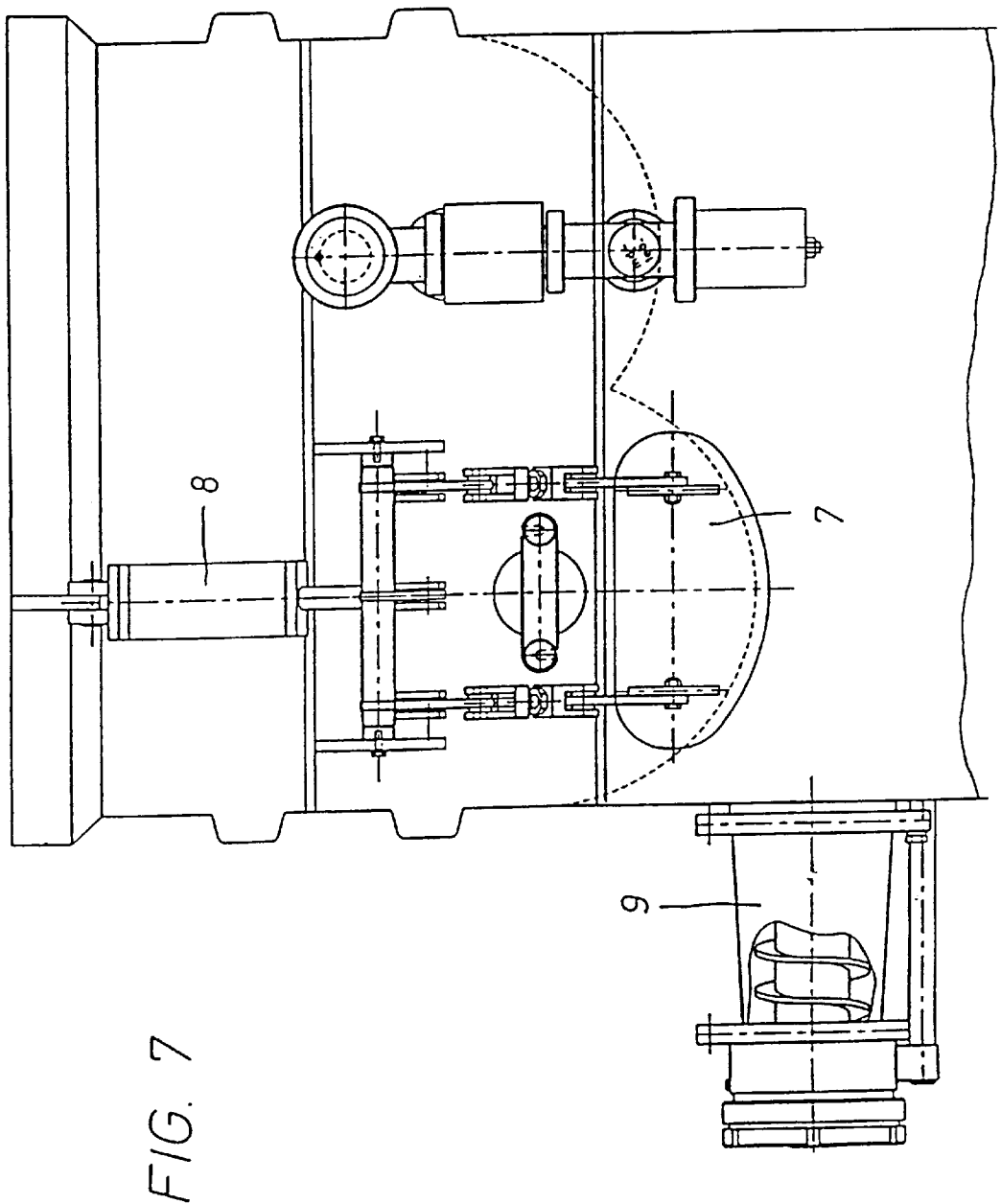

In the following detailed portion of the present description, the invention will be explained in more detail with reference to the drawings, in which FIG. 1 shows an embodiment of an apparatus according to the invention for examining a flowable material, FIG. 2 shows a variation of the embodiment of FIG. 1 comprising a light-conducting cable, FIG. 3 shows another embodiment of the apparatus according to the invention comprising laser diodes, FIG. 4 is a graph showing the transmittance as a function of wavelength of meat samples with high-and low fat content, respectively, having been measured in the equipment shown in FIG. 1, FIGS. 5a–5f show various operating positions of a device according to the invention for conveying a material being used in connection with the apparatus of FIG. 1, and FIGS. 6 and 7 show how the apparatus and the device are mounted on a mixer.

The measuring device in FIG. 1 comprises a tube segment 10b serving as a measuring chamber in connection with the measurement of the transparency of a meat material to infra-red light at various wavelengths. For this purpose, it comprises two windows 24 made of glass or other transparent material inserted in cut-outs in the tube wall facing each other. A measuring device or housing 25 with various means for measuring the transparency of the material present between the windows 24 is placed on the tube section 10b. A broad-spectrum light source 32 emits light within the operating range, in the present case the near-infra-red interval between 700 and 1200 nm. The light source 32 comprises or constitutes a tungsten-halogen lamp emitting a major proportion of the input of electrical energy in the infra-red spectral range and having a power rating of between 20 and 70 W or more, e.g. 100 W.

Adjacent to the light source 32 there is a preferably elliptical or parabolic reflector 33 directing the light mainly towards the right. A rotatable filter disc 34 with 6–20, e.g. 12, different filters 35 is placed between the light source 32 and the windows 24 in the tube segment 10b, each of said filters 35 allowing passage of light of a respective wavelength interval through the windows 24 in the tube segment 10b. The narrow-band light entering through the left-hand window passes through the material in the tube suffering a substantial loss and exits through the right-hand window, after which it impinges upon a wide-spectral photo-detector 36, e.g. a plate assembled from a number of Si wafers.

The attenuation of the light in the material is due to the absorption caused by the various components of the material as well as the dispersion and reflection of the light as a consequence of phase transitions or particles in the material. The absorption depends on the components and the wavelength.

Thus, the photo-detector 36 will produce signals depending on the content of components in the material being measured and the wavelength. The signal is amplified, filtered, digitized and stored in an electronic memory. The windows 24 and the beam path are dimensioned in such a manner, that the detector 36 receives light having passed through a volume of material of more than 100 ml. The volume of material corresponds to the volume of the space between the windows 24.

The measuring device comprises a motor 37 for rotation of the filter disc 34, so that the filters 35 one by one can be placed in the beam path between the light source 32 and the detector 36. Each time a new filter has been placed in the measuring position, the signal from the detector 36 is recorded and stored, said signal having a strength depending on the absorption in the wavelength interval of the filter of the material being measured. When measurement values have been recorded and stored for all filters in the disc 34, the measuring is complete. After this, the removal of material from the region between the windows may be initiated.

In the embodiment shown in FIG. 2, the light source 32 is placed in a separate enclosure. The light is conducted via a lens 38 through a fibre cable 39, from the far end of which it radiates against the filter 35. The photodetector 36 is the same as in FIG. 1, but a corresponding arrangement with a light-conductor cable may, if so desired, be placed on the detector side.

Instead of using one wide-spectrum light source with a rotatable filter disc in front, it is possible to use monochromatic or narrow-band, discrete light sources, each emitting light at a respective wavelength. FIG. 3 shows such an embodiment, using laser diodes instead of the lamp and the filter disc. The arrangement of FIG. 3 has the advantage of having no moving parts.

The arrangement of FIG. 3 comprises a number of (power) laser diodes 40, each emitting light of a respective wavelength towards the material sample. Typically, 4–20 diodes are used, placed on the same chip. Each laser diode emits light of a respective wavelength within the range from 800–1050 nm, so that the use of filters is not necessary. For sensing the light having passed through a sample of thickness 5–10 cm a PMT detector 41 is used. By activating one diode at a time it is possible by means of the detector 41 to measure how much light penetrates through the sample at the various wavelengths.

FIG. 4 shows the signal from the detector 36 of FIG. 1 during one revolution of the filter disc 34. The fully drawn curve represents a finely minced sample of pork with a fat content of approximately 50%. The sample is placed in the tube segment 10b. The lightly drawn curve has been recorded with a finely minced sample of beef with approximately 5% fat. The samples attenuate the light approximately 4000 times. The peak values represent the transmittance at the 11 different wavelengths. It can be seen that the samples attenuate the light differently at the various wavelengths because of the differences in fat and water content in the samples, this being used for computing these values.

Based on the stored measurement values, a data processing unit automatically computes the content of e.g. fat in the material, said unit having been provided with a program with the necessary computing routines.

In the embodiment shown having a measuring volume between 60 and 400 ml (e.g. between 200 and 400 ml) being used for making measurements on coarsely comminuted meat material, one single result does not provide the requisite certainty, for which reason it is necessary to introduce new material and carry out the measuring cycle a number of times, e.g. 10 times, until the measurements have covered a representative quantity, making it possible to compute the fat content on the basis of the sum total of the measurement values with the necessary certainty.

If the material is uniform in nature, e.g. as in the case of finely minced meat or meat emulsions, satisfactorily accurate results may be achieved by only carrying out a single measuring cycle.

By means of the stored measurement values, it is possible to determine the content of various components in the material, e.g. fat, protein, collagen and water. If a number of sets of measuring values, each having been obtained by means of a respective measuring cycle, are used, a substantial improvement of the accuracy of the result will be achieved, which is of special importance when the quantity being measured in each cycle is not representative.

The samples being measured in the apparatus of FIG. 1 may be removed from and introduced in the measuring segment 10b of the tube 10 by means of the device shown in FIGS. 5a–5f, illustrating different operating positions in an operating cycle.

The device comprises a tube segment 10b, being the same as the tube segment 10b of FIG. 1. By means of flanges 11, the tube segment 10b is connected to two other tube segments 10a and 10c, that are angular so that the tube 10 formed by the three segments 10a, 10b and 10c consists of a vertical central part and two horizontal end parts. As may be seen from FIGS. 6 and 7, the device is mounted on a mixing tank 2. In the vertical wall of this tank to the left in FIG. 6 and close to the bottom, an opening has been cut to fit the lowermost horizontal end part of the tube, and at a level above the shaft 3, a second opening is cut to fit the upper horizontal parts of the tube. By means of flanges 12 on the end part, the tube 10 is secured to the tank opposite the openings, so that material by itself will flow into the lower tube segment 10a and may be returned to the tank by means of a conveying arrangement.

The plant shown in FIGS. 6 and 7 comprises a usual mixer 1 with a mixing tank 2, adapted to accommodate between 500 and 6000 kg meat material according to need. In the tank 2, there are two mixing devices consisting of two mutually parallel shafts 3 with radial rods carrying blades 4. The mixing devices may be rotated in both directions by means of a motor arrangement 5. The arrangement is controlled by means of a control panel 6 on which an operator inputs the mixing program suitable for the production in hand.

In the end of the tank 2 opposite the motor arrangement there is a discharge opening provided with a trap door 7 (FIG. 7) that may be opened and closed by means of a pneumatic cylinder 8. The bottom of the tank is indicated with an arched dotted line. During discharge, the material tends to collect in the deeper left-hand part of the tank, in which it is "shovelled" forward towards the discharge opening by the mixing device.

On one side, the tank 2 carries a worm conveyor 9, providing an additional possibility of discharging material from the tank. The worm conveyor 9 may be terminated by a perforated disc with a rotating set of knives adapted to comminute the material during the discharge. EP-A-0,569,854 (WOLFKING DANMARK A/S) comprises a description of such a type of mixing machine.

A control unit 6a situated below the control panel 6 serves to control the functions of the plant and to receive and process data from the measuring device 25 on the tube 10, e.g. signals expressing the fat content of the sample. Signalwise, the unit 6a is connected to the control panel 6 of the mixer 2, so that the processed data from the apparatus can be displayed to the operator or used for automatic monitoring and control of the mixing program contained in the control panel.

On the lowermost tube segment 10a (FIG. 5a), the device for taking samples from the container 2 comprises a cylinder 14 mounted by means of a flange 13 and closed at the lower end. In the cylinder 14, there are two pistons 15 and 16. The upper piston 15 comprises a short tube 17 capable of sliding in a lowermost vertical part of the tube segment 10a, while the lower piston 16 carries a plunger 18 having an outer diameter corresponding to the inner diameter of the short tube 17, so that the plunger slides within the short tube. The black areas in FIGS. 5a–5f represent gaskets providing seals between movable parts.

Below the piston 16 there is a coupling part 21 for connecting a compressed-air tube or hose. For the sake of simplicity and ease of understanding, compressed-air tubes or hoses and their connections to control valves are not shown in the Figures.

Via the coupling part 21, air under pressure may be introduced into the interspace between the pistons 15 and 16, so that the piston 15 is made to move upwardly. Coupling parts 22 and 23 for the connection of compressed-air tubes or hoses are also provided in the bottom of the cylinder 14 and in the flange 13 constituting the top of the cylinder.

As mentioned before, the central part of the tube segment 10b serves as a measuring chamber in connection with measurements of the transparency of the meat material to infra-red light of various wavelengths.

The upper tube segment 10c comprises a flange 26 carrying a cylinder 27 closed at one end. In the cylinder there is a movable piston 28, on the right-hand side of which is mounted a plunger 29 adapted to slide within the horizontal part of the tube segment 10c. In the bottom of the cylinder 27 there is a coupling part 30 for a compressed-air tube, and the flange 26 comprises a similar coupling part 31 for compressed air.

The functioning of the device will now be described in more detail.

Different types of un-analysed raw materials, having been coarsely comminuted and then placed in respective storage tubs, are weighed and introduced into the tank 2 (FIG. 6). For a short time, the raw materials are mixed in the tank by rotating the mixing device. The control unit 6a controls the valves on the compressed-air tubes connected to the device through the coupling parts 21, 22, 23, 30 and 31 in such a manner, that the pistons 15, 16 and 28 take up the positions shown in FIG. 5a. After this, the mixing devices are made to rotate in such a direction, that the material below in the tank is urged towards the opening close to the bottom of the tank and out through the opening and into the lower tube segment 10a. In the figures, the material is indicated by means of dotted areas.

When the pressure of the material against the opening is at a maximum, i.e. when a blade 4 is opposite the opening, the following sampling and measuring procedure is initiated:

Compressed air is admitted to the space between the pistons 15 and 16, causing the piston 15 with the short tube 17 to move upward to an upper abutment position shown in FIG. 5b, in which the short tube 17 entraps the material having been forced into the vertical part of the tube by the mixing devices, the tube already having been closed at the top by the plunger 29.

Now, the entrapped material is compressed by compressed air being admitted into the space between the bottom of the cylinder 14 and the piston 16 via the coupling part 22, so that the piston 16 with the plunger 18 is moved upwardly while reducing the space available for the entrapped material. In the simultaneously decreasing space between the piston 15 and the piston 16, the pressure is equalized by means of the duct 20 and a counter-pressure valve placed on the latter's compressed-air tube and adjusted to a certain pressure.

When starting-up the plant, i.e. when carrying out the first cycle, the vertical part of the tube 10 mainly contains air, for which reason the piston 16 with the plunger 18 moves upwardly to an uppermost position, in which the piston 16 abuts against the lower side of the piston 15. After a few cycles have been carried out, the vertical part of the tube 10 will, however, mainly contain meat material and only a lesser proportion of air. This is the operating situation now to be described.

In the operating state, the piston 16 with the plunger 18 will only move to an intermediate position exemplified in FIG. 5c. In this position there is equilibrium between the pressure in the entrapped material and the upwardly directed force exerted by the piston 16. Compression is carried out to a relatively high pressure in order to reduce or eliminate the influence of the air on the measurements being made on the material between the windows 24. With the transverse dimension of the piston 16 and the plunger 18, a pressure amplification of five times is achieved, so that a pressure in the material of 1250 kPa (12.5 bar) is provided, if the compressed air is adjusted to a pressure of 250 kPa (2.5 bar).

After the material thus having been compacted in the vertical part of the tube 10, measurements are carried out on the transparency of the material between the windows 24 at a number of wavelengths in the infra-red range, and the results are used for computing one or a number of properties of the material. The construction and functioning of the measuring device 25 has already been described in connection with the explanation of FIG. 1.

When the measurements have been carried out, the pressure in the vertical part of the tube 10 is equalized with atmosphere by moving the piston 28 with a plunger 29 towards the right, compressed air being admitted on the right-hand side of the piston via the coupling part 31. When the vertical part of the tube 10 is opened at the top, the material can expand from here out into the horizontal part of the tube in the tube segment 10c and from there out into the tank 2. As soon as the pressure in the vertical part of the tube 10 falls, the piston 16 with the plunger 18 is forced to the uppermost position shown in FIG. 5e, causing additional material to be removed from the vertical part and to be forced out into the tank 2.

When the piston 28 with the plunger 29 has reached the extreme left-hand position, the piston is reversed towards the initial right-hand position, compressed air being admitted on the left-hand side of the piston via the coupling part 30 at the same time as the pressure is removed on the right-hand side of the piston. During the reverse movement, the plunger 29 forces material out from the upper horizontal part of the tube in the segment 10c and back into the tank 2.

Material having been admitted into the tube segment 10a through the opening close to the bottom of the tank will in this manner be returned to the tank 2. During the reverse movement, the plunger 29 will again close the vertical part of the tube 10 at the top, as may be seen from FIG. 5f.

After this, the piston with the short tube 17 and the piston 16 with the plunger 18 will be moved towards their lowermost positions, pressure being applied to the upper side of the piston 15 via the compressed air conduit secured to the coupling part 23. During the movement, in which the short tube 17 and the plunger 18 are pulled downwardly in the vertical tube, the increase in volume will create a subatmospheric pressure. In the final part of the movement of the short tube 17, passage is created between the vertical part of the tube and the lower horizontal end part in the tube segment 10a, so that material will be sucked into the vertical part of the tube. The opening of the passage preferably occurs simultaneously with a blade 4 being opposite to the opening close to the bottom of the tank 2, so that at the same time, the material will be subjected to suction on one side and pressure on the other side. In this manner, new material is introduced into the tube segment 10a.

When the pistons 15 and 16 have reached their lowermost positions and the piston 28 is in its extreme right-hand position (FIG. 5a), a portion of material in the vertical part of the tube will again have been expelled out into the tank 2 and a new portion of material will have been taken in from the bottom of the tank for successive compression and measuring in the vertical part of the tube 10, thus completing a working cycle. This working cycle may immediately be succeeded by new and similar working cycles in a given rhythm, e.g. one per second (making the cycle time one second). The inside diameter of the vertical part of the tube 10 and the stroke volume of the plunger 18 may e.g. be dimensioned in such a manner, that each working cycle brings between 60 and 400 ml new material into the tube. After one or a few working cycles, the new material will have been introduced into the space between the windows 24, after which measurements may be carried out.

By repeating the measurements on new portions of material being introduced into the space between the windows 24, so many measuring data will finally be obtained that the measurements as a sum total are representative, and the fat content in the coarsely comminuted material may be determined with the requisite accuracy. The quantity of material necessary for a representative measurement depends on the type and particle size of the material.

Further, the measurement values from each sampling and measuring cycle may be used to check whether the material is processed in an optimum manner, e.g. whether a mixing process is sufficiently thorough. The fat content of the material may e.g. be computed each time a sample is taken and measured, and the result compared with the previous result or the average of a number of immediately preceding results. If a great deviation is found, this is a sign that the material in e.g. the mixing tank is still heterogeneous, and that the mixing process should continue. If the deviation is only a minimum or lies below a predetermined limit, it is not possible to improve the homogeneity of the material by continuing the mixing process, for which reason it is terminated. In this manner, it is normally possible to shorten the mixing process to what is strictly necessary, and the material is saved from being subjected to continued mechanical processing.

Instead of using the deviation to control the mixing time, the standard deviation of the results may be used. If the computed standard deviation for the most recent cycles falls below a predetermined level, or if it is not improved by continuing the mixing process, this is a sign that the mixing process should be terminated.

Already before the material exhibits the desired homogeneity, it will in many cases be possible to determine the fat content or the like with a satisfactory accuracy, e.g. based on the tendency of the results to approach a final value. Thus, it may be possible at a relatively early stage in the mixing process to predict how much fat-containing meat product is to be added to the material in the tank in order that the finished mixed product will comply with the specifications. For this reason, the plant makes it possible to adjust the material quickly, thus contributing to ensure that the material is not subjected to mechanical processing longer than necessary to achieve a homogeneous mixture. When the measurements have shown that the material in the mixing tank exhibits the desired homogeneity, a final check on the fat content may be made on the basis of the measuring results from the most recent measuring cycles.

It is possible to adjust the material during the mixing process by adding fat-containing material, this making it possible for the finished mixed material to comply with strict specifications or be close to an optimum fat content within given specifications, without necessarily increasing the mixing time. The addition of fat-containing material in connection with the adjustment may take place manually or automatically.

All these computations and evaluations may be carried out automatically by the control unit 6a on the basis of measuring data received. When this unit by means of an included program e.g. finds the results to be stable, it can automatically signal to the control panel 6 that the mixing operation is finished as far as homogeneity is concerned, after which the control panel itself or an operator having observed a signal from it may stop the motor arrangement driving the mixing devices.

With the embodiment having been described above, the measurements are carried out using near-infra-red radiation. It is also possible, however, to examine the material being advanced in the tube 10 by means of other types or a number of different types of electromagnetic energy. E.g. a further tube segment may be inserted downstream of the tube segment 10b and having measuring devices for determining the content of liquid water in the material by means of microwave energy. In that case, the content of ice in the material may be determined as the difference between the water percentage determined by means of near-infra-red measurement in the tube segment and the water percentage determined by means of microwave measurements.

What is claimed is:

1. Device for conveying samples in connection with the examination of a flowable material, comprising:
    a) a tube having:
        i) a first opening for receiving a material,
        ii) a second opening for discharging said material, and
        iii) a tube segment between said openings for holding said material for examination;
    b) a movable first closure comprising a tube capable of sliding in the tube segment disposed in said tube segment at the first opening for receiving material;
    c) conveying means for moving material received through said first opening to said tube segment, wherein the material is moved into the tube segment without first completely emptying the tube segment of all material already present therein; and
    d) a second closure comprising a plunger disposed in said tube segment between said tube segment and said discharge opening, said second closure being movably mounted for movement to a closed position during a period while said conveyor moves said material into said tube segment.

2. Device according to claim 1, wherein said first closure is movably mounted for movement to an opened position for reception of material through said first opening and to a closed when said material received through said first opening is conveyed to said tube segment.

3. Device according to claim 1, wherein said second closure is mounted for movement to an opened position after said material has been examined and is to be moved out of said tube segment.

4. Device according to claim 1, wherein said conveying means includes a plunger slidably mounted in a fluid-tight manner in said tube.

5. Device according to claim 1, wherein at least one pneumatic cylinder with piston is connected to at least one of said conveying means and closures for controlling their movement.

6. Device according to claim 1, wherein said conveying means includes means for compacting the material in a direction parallel to the flow of material through the tube at a pressure of more than 200 kPa.

7. Device according to claim 1, wherein said conveying means includes means for compressing said material when in said tube segment before examination is carried out, to a pressure of between 200 and 2000 kPa.

8. The device of claim 1 adapted to examine flowable material, with the first opening receiving the flowable material, and the device further comprises a measuring device disposed adjacent to the tube segment, wherein the tube segment has opposite side walls, the measuring device having i) a light source adjacent one side wall of the tube segment to transmit light of a predetermined wavelength range along a beam path and through said tube segment and ii) a light receiver adjacent the opposite side wall of the tube segment to measure the effect upon said light transmitted along said beam path of said material when placed in said tube segment, wherein the side walls of said tube segment are aligned with the beam path between the light source and the light receiver and are made of a material that is translucent or transparent for said wavelength range of the light to be examined; a recording unit connected to said measuring device and adapted to record individual measurement values or sets of measurement values for said material placed in said tube segment; and conveying means for conveying said material received through said first opening to said tube segment, wherein said conveying means comprises a plunger adapted to slide in a fluid-tight manner inside the tube in the direction of flow of the material.

9. The apparatus of claim 8 wherein the plunger is adapted to be displaced through said tube segment wherein the side walls of said tube segment align with said beam path between the light source and the light receiver, thereby positively displacing said flowable material from the tube segment.

10. The apparatus of claim 8, further comprising a movable second closure disposed in said tube between said tube segment and said discharge opening, wherein said first closure is movably mounted for movement to an opened position for reception of material through said first opening and to a closed position when said material received through said first opening is conveyed to said tube segment, and wherein said second closure is movably mounted for movement to a closed position during a period while said conveyor moves said material into said tube segment.

11. The apparatus of claim 10, wherein said second closure is mounted for movement to an opened position after said material has been examined and said material is to be moved out of said tube segment.

12. The apparatus of claim 10, further comprising a pneumatic cylinder with piston operably connected to said plunger, wherein said pneumatic cylinder and piston are adapted for controlling movement of the plunger.

13. The apparatus of claim 10, wherein said conveyor includes means for compressing said material when in said tube segment before examination is carried out, to a pressure of between about 200 and about 2000 kPa.

14. The apparatus of claim 10, wherein the discharge opening is operatively connected to the process, such that material discharged from the discharge opening re-enters the process.

15. The apparatus of claim 10, wherein the apparatus is adapted to measure the transmittance or absorption of said material in said tube segment at a number of wavelengths in the range from 700 to 2400 nm.

16. The apparatus of claim 8, wherein the movable first closure and wherein the movable second closure can be in the opened position at the same time, and wherein the conveyor is adapted to continuously move material from the first opening, through the tube, and out the second opening.

17. The apparatus of claim 8, wherein the said tube is dimensioned in such a manner that said light beam path has a length through said material when placed in said tube segment is between about 40 mm and about 100 mm.

18. The apparatus of claim 8, wherein said light receiver is a detector plate sensitive for light in a wide spectrum having an effective area between about 500 and about 10000 $mm^2$.

19. The apparatus of claim 8, wherein
  a) said light source and the light receiver are of the wide-spectrum type;
  b) a rotatable filter disc mounted on a shaft is disposed in the beam path between the light source and the light receiver, said rotatable filter disc having cut-outs placed at uniform distances from each other; and
  c) filters are disposed in each of said cut-outs, each filter allowing a respective wavelength interval to pass, whereby one filter at a time can be placed in the beam path by means of rotating said shaft by way of a motor.

20. The apparatus of claim 8, wherein said light source consists of a number of monochromatic laser diodes, wherein each is adapted to emit a specific wavelength interval within the range between 700 and 1200 nm.

21. The device of claim 1, adapted to convey a material that is a minced or cut meat product.

* * * * *